(12) United States Patent
Stieghorst et al.

(10) Patent No.: US 11,235,164 B2
(45) Date of Patent: Feb. 1, 2022

(54) SHAPE-ADAPTIVE MEDICAL IMPLANT

(71) Applicant: MEDIZINISCHE HOCHSCHULE HANNOVER, Hannover (DE)

(72) Inventors: Jan Stieghorst, Nienhagen (DE); Theodor Doll, Bochum (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 367 days.

(21) Appl. No.: 16/305,458

(22) PCT Filed: May 30, 2017

(86) PCT No.: PCT/EP2017/063024
§ 371 (c)(1),
(2) Date: Nov. 29, 2018

(87) PCT Pub. No.: WO2017/207561
PCT Pub. Date: Dec. 7, 2017

(65) Prior Publication Data
US 2020/0324124 A1  Oct. 15, 2020

(30) Foreign Application Priority Data

Jun. 1, 2016  (DE) .................... 10 2016 110 137.0

(51) Int. Cl.
| | | |
|---|---|---|
| A61N 1/375 | (2006.01) | |
| A61N 1/36 | (2006.01) | |
| A61N 1/04 | (2006.01) | |
| A61N 1/05 | (2006.01) | |

(52) U.S. Cl.
CPC ......... *A61N 1/3758* (2013.01); *A61N 1/0444* (2013.01); *A61N 1/0541* (2013.01); *A61N 1/36038* (2017.08)

(58) Field of Classification Search
None
See application file for complete search history.

(56) References Cited

U.S. PATENT DOCUMENTS

| | | | | |
|---|---|---|---|---|
| 5,545,219 A | * | 8/1996 | Kuzma | ..................... A61N 1/05 623/10 |
| 5,578,084 A | * | 11/1996 | Kuzma | ................. A61N 1/0541 607/137 |
| 5,653,742 A | * | 8/1997 | Parker | ...................... A61D 7/00 607/116 |

(Continued)

FOREIGN PATENT DOCUMENTS

| | | |
|---|---|---|
| EP | 1 790 380 A1 | 5/2007 |
| WO | 2015/030734 A1 | 3/2015 |
| WO | 2015/188805 A1 | 12/2015 |

*Primary Examiner* — Carl H Layno
*Assistant Examiner* — Manolis Pahakis
(74) *Attorney, Agent, or Firm* — W&C IP

(57) ABSTRACT

The invention relates to a shape-adaptive medical implant having at least one actuator, which the implant can be changed from a first implant geometry to a second implant geometry, the implant having a different geometric shape in the second implant geometry from that in the first implant geometry, wherein the actuator has a swellable chemical substance which swells when supplied with liquid, and wherein the implant which is designed to supply liquid present outside the implant to the swellable chemical substance. The invention also relates to the use of an electrical signal source.

11 Claims, 2 Drawing Sheets

(56) References Cited

U.S. PATENT DOCUMENTS

| | | | | |
|---|---|---|---|---|
| 5,800,500 A * | 9/1998 | Spelman | ............... | A61N 1/0541 607/137 |
| 5,876,443 A * | 3/1999 | Hochmair | ............. | A61N 1/0541 623/10 |
| 6,074,422 A * | 6/2000 | Berrang | ............... | A61N 1/0541 607/137 |
| 7,269,461 B2 * | 9/2007 | Dadd | ................... | A61N 1/0541 607/137 |
| 7,272,449 B2 * | 9/2007 | Dadd | ................... | A61N 1/0541 607/137 |
| 7,406,352 B2 * | 7/2008 | Gibson | ................ | A61N 1/0541 607/137 |
| 8,145,326 B2 * | 3/2012 | Abbasi | ................. | A61N 1/0541 607/137 |
| 8,473,075 B2 * | 6/2013 | Gallegos | ............. | A61N 1/0541 607/137 |
| 8,843,216 B2 * | 9/2014 | Wallace | ............... | A61N 1/0541 607/137 |
| 9,089,450 B2 * | 7/2015 | Gibson | ................ | A61N 1/0541 |
| 9,375,565 B2 * | 6/2016 | Pawsey | ................ | A61N 1/0541 |
| 2002/0029074 A1 * | 3/2002 | Treaba | ................ | A61N 1/0541 607/137 |
| 2003/0065373 A1 * | 4/2003 | Lovett | ................... | A61N 1/056 607/122 |
| 2003/0078516 A1 * | 4/2003 | Abbasi | ................. | A61N 1/0541 600/559 |
| 2003/0093139 A1 * | 5/2003 | Gibson | ................ | A61N 1/0541 607/137 |
| 2005/0043765 A1 * | 2/2005 | Williams | .............. | A61N 1/057 607/9 |
| 2006/0036307 A1 * | 2/2006 | Zarembo | ................ | A61N 1/056 607/122 |
| 2006/0058861 A1 | 3/2006 | Gibson et al. | | |
| 2007/0225564 A1 * | 9/2007 | Couvillon | ............. | A61B 1/012 600/140 |
| 2008/0103573 A1 * | 5/2008 | Gerber | ................ | A61N 1/0536 607/116 |
| 2009/0062896 A1 * | 3/2009 | Overstreet | .......... | A61N 1/0541 607/137 |
| 2009/0254163 A1 * | 10/2009 | Gibson | ................ | A61N 1/0541 607/137 |
| 2009/0259280 A1 | 10/2009 | Wilkin et al. | | |
| 2011/0106101 A1 | 5/2011 | Tortonese et al. | | |
| 2011/0237921 A1 * | 9/2011 | Askin, III | ................ | A61B 5/25 600/377 |
| 2011/0319907 A1 | 12/2011 | Gallegos et al. | | |
| 2012/0123318 A1 * | 5/2012 | Ek | ........................... | A61L 31/16 604/20 |
| 2013/0131482 A1 * | 5/2013 | Fedder | ................... | B29C 41/42 600/378 |
| 2015/0045867 A1 * | 2/2015 | Krishnan | ................. | A61N 1/05 607/119 |
| 2015/0164401 A1 * | 6/2015 | Toth | ..................... | A61B 5/0036 600/301 |
| 2015/0369771 A1 | 12/2015 | Richardson-Burns et al. | | |
| 2016/0128767 A1 * | 5/2016 | Azamian | ............ | A61B 18/1492 606/41 |
| 2016/0213913 A1 * | 7/2016 | Dhanasingh | ......... | A61N 1/0541 |
| 2018/0169399 A1 * | 6/2018 | Housley | ................... | A61N 1/08 |
| 2018/0289950 A1 * | 10/2018 | Bedenbaugh | ........ | A61N 1/0529 |
| 2020/0324124 A1 * | 10/2020 | Stieghorst | ........... | A61N 1/3758 |

* cited by examiner

SHAPE-ADAPTIVE MEDICAL IMPLANT

FIELD OF THE INVENTION

The invention relates to a shape-adaptive medical implant comprising at least one actuator by means of which the implant can be shifted from a first implant geometry to a second implant geometry, the implant having a different geometric shape in the second implant geometry than in the first implant geometry, the actuator having a swellable chemical substance which swells as a consequence of supply of liquid, and the implant having at least one liquid-transport means which is configured to supply liquid present outside the implant to the swellable chemical substance. The invention additionally relates to the use of an electrical signal source as claimed in claim 10. The invention thus relates to the field of medical implant treatment using shape-adaptive elements, especially plastics implants in general.

BACKGROUND

Medical implants are used in a multiplicity of applications. In some applications, it is necessary for the implant in a particular hollow area of the body to match particularly well with the geometry of the hollow area, for example in the case of cochlear implants with the shape of the cochlea. For example, for such an application, WO 2015/188805 A1 discloses a self-bending implant in which a polymer capable of swelling is present in a base body of the implant.

Flexible plastics implants are typically used in contact with soft-tissue structures such as, for example, hollow organs or nerve structures. On the basis of their structure and their combination of materials, the aim is to achieve a best possible match with the recipient tissue and to minimize the tissue damage arising upon implantation. Common soft-tissue implants therefore usually consist of a highly flexible elastomer base body, which, in the case of an active implant, is additionally provided with conductor structures, such as platinum wires for example, for electrical stimulation. A known representative for this purpose are cochlear implant systems (CI), which are used in the inner ear in the case of lost stimulus transduction (sensorineural hearing loss). To restore hearing, an electrode support is implanted into the inner ear and the nerve cells are electrically stimulated. For a better matching of the electrode supports with the nerve structures, use is made of preshaped electrode supports which have the snail shape of a typical cochlea. To be able to insert the electrode supports during implantation, the electrode support must be kept straight with a small, embedded metal wire (stylet). With increasing depth of insertion, the metal wire is drawn and the electrode moves back into its predefined shape. Research approaches which have not been implemented to date follow the use of shape memory metals and swelling polymers [U.S. Pat. No. 8,145,326 B2], which, in the latter case, are intended to press the electrode support through repulsion on the lateral side in the direction of the nerve cells (perimodiolar position).

SUMMARY OF THE INVENTION

It is an object of the invention to design such shape-adaptive medical implants to be more practical and to be more gentle for patients.

In the case of the shape-adaptive medical implant mentioned at the start, this object is achieved by one of, a plurality of or all of the following features a), b), c), d):

a) the implant has an electrical signal-delivery arrangement suppliable with electrical signals and comprising an arrangement of electrical conductors and/or electrodes, which is configured to supply the swellable chemical substance of the actuator with an electric and/or electromagnetic field, the swellable chemical substance being configured to convert from the swollen state into the nonswollen state as a consequence of its supply with the electric and/or electromagnetic field by the electrical signal-delivery arrangement, b) the implant has a liquid-tight sealing means composed of a liquid-soluble chemical substance which seals the liquid-transport means in a liquid-tight manner, c) the implant, more particularly its actuator, has lateral limiting means, by means of which the lateral expansion of the implant and/or of the actuator as a consequence of the swelling of the swellable chemical substance is limited, d) the actuator, more particularly the swellable chemical substance, contains an ionic medicament for the specific delivery of active ingredient after implantation of the implant in the body.

The invention has the advantage that, in accordance with feature a), the explanation behavior of the implant is improved. If, in the event of a revision operation, the implant must be removed from the body into which it was implanted, this can be done such that, as a result of delivery of electrical signals to the swellable chemical substance situated in the swollen state, it is brought to the nonswollen state again. Accordingly, the implant can be removed essentially without tissue damage.

In this way, the implant can be in the form of an electrically actuatable or electrically switchable medical implant. The second implant geometry can, in particular, be a curved geometric shape. As a result of the reduction in swelling of the swellable chemical substance, the implant can, in particular, assume the first implant geometry again or another geometric shape differing from the second implant geometry.

The liquid which swells the swellable chemical substance can, for example, be water or an aqueous substance, more particularly aqueous substances in the human body. In the case of a cochlear implant, the liquid can be an aqueous intracochlear liquid which is situated in the cochlea.

The invention has the advantage that, in accordance with feature b), the supply of liquid to the swellable chemical substance can be done in a defined manner. The liquid-tight sealing means can, for example, be introduced in an implant base body close to the edge in the form of small particles and dissolve upon contact with the liquid. The sites which become available in the course of this form, in the case of an appropriately small particle size of the dissolving liquid-soluble chemical substance, a porous membrane structure at the implant base body, which membrane structure satisfies the desired separation properties between the liquid outside the implant and the actuator filled with the swellable chemical substance. Thus, the swellable chemical substance cannot leave the actuator, but liquid can get into the interior of the actuator from the outside through the membrane structure and thus bring about the swelling of the swellable chemical substance.

The invention has the advantage that, in accordance with feature c), the contact pressure of the implant on a hollow structure in the body can be limited, for example the contact pressure in the cochlea. In this way, it is possible to avoid undesirably high contact pressures and corresponding associated risks as a result of the swelling of the swellable chemical substance. The lateral limiting means limits the lateral expansion, in other words the expansion in the radial direction, for example to a predefined maximum extent of the implant or, flexibly, to a maximum contact pressure.

The invention has the advantage that, in accordance with feature d), the implant can, at the same time, be used for delivering active ingredients in a specific manner into the body provided with the implant. Under the influence of an electric field, the medicament can, for example, be delivered in specific doses into the surrounding liquid.

According to an advantageous further development of the invention, the swellable chemical substance is, or at least predominantly comprises, a polyelectrolytic hydrogel. In this way, it is possible to provide a biocompatible swellable chemical substance. Moreover, the polyelectrolytic hydrogel is convertible in a reversible manner from the swollen state into a nonswollen state once again, specifically by application of an electric field to the polyelectrolytic hydrogel.

According to an advantageous further development of the invention, the liquid-transport means has a membrane-type structure and/or micropores of the outer skin of the actuator. In this way, the outer skin of the actuator is permeable for the liquid which is to penetrate into the interior of the actuator from the outside in order to allow the swellable chemical substance to swell. At the same time, the swellable chemical substance cannot escape from the actuator.

According to an advantageous further development of the invention, the liquid-soluble chemical substance of the liquid-tight sealing means is, or at least predominantly comprises, polyvinylpyrrolidone. In this way, a biocompatible liquid-soluble chemical substance is provided as liquid-tight sealing means. Appropriate polyvinylpyrrolidone preparations are, for example, available under the trade name Luvitec from BASF.

According to an advantageous further development of the invention, the implant, more particularly its actuator, has a fiber reinforcement which is integrated into the outer skin or is attached thereto. Such a fiber reinforcement can shape the actuator more robustly. Moreover, the fiber reinforcement can realize the lateral limiting means. The fiber reinforcement can, in particular, be arranged on the actuator close to the surface or be integrated into the material of the actuator, i.e., its shell. The fibers can, for example, be in the form of threads or wires.

According to an advantageous further development of the invention, the fiber reinforcement is in the form of a unidirectional fiber reinforcement, more particularly in the form of a unidirectional fiber reinforcement running with its fiber direction in the transverse direction of the actuator. Such a fiber direction and type of fiber reinforcement can, in particular, realize a desired longitudinal expansion of the actuator with limited lateral expansion.

According to an advantageous further development of the invention, the electrical signal-delivery arrangement is formed at least in part by electrically conductive fibers of the fiber reinforcement. This has the advantage that the integration of the electrical signal-delivery arrangement in the implant is simplified, and that there is no need for additional elements apart from the fibers of the fiber reinforcement in order to realize the electrical signal-delivery arrangement. The electrically conductive fibers of the fiber reinforcement can, for example, be in the form of carbon fibers.

According to an advantageous further development of the invention, the fibers of the fiber reinforcement have a linked structure. This creates a structure which realizes the lateral limitation of the expansion of the actuator without suppressing the desired stretching in the longitudinal direction (axial direction).

According to an advantageous further development of the invention, the implant is in the form of a cochlear implant which has, in addition to the electrical signal-delivery arrangement, an electrode support on which stimulation electrodes for the stimulation of the cochlea are arranged. In this way, it is possible to provide a cochlear implant which is particularly gentle for patients and highly functional. Advantageously, the stimulation electrodes and/or their electrical lines can, at the same time, form the electrical signal-delivery arrangement or at least a part thereof.

The object mentioned at the start is further achieved by the use of an electrical signal source to supply the electrical signal-delivery arrangement of a medical implant of the above-elucidated type with electrical signals in order to explant the implant from a state implanted in the body. This, too, can realize the above-elucidated advantages. The electrical signal source can be an electrical signal source of any type, for example a direct current source, a DC voltage source or a signal source which delivers an electrical alternating signal.

Using the implant according to the invention, it is, for example, possible to realize the following method.

Method for explaining a medical implant of the above-elucidated type from a state implanted in the body, comprising the following steps:
a) connecting the electrical signal arrangement of the implant to an electrical signal source,
b) supplying the chemical substance in the actuator with electrical signals via the electrical signal arrangement over an exposure time,
c) removing the implant from the body after the exposure time.

This, too, can realize the above-elucidated advantages.

BRIEF DESCRIPTION OF THE DRAWINGS

The invention will be more particularly elucidated below on the basis of exemplary embodiments with use of drawings, where.

The figures use the same reference signs for elements which correspond to one another.

DETAILED DESCRIPTION

Figure 1:
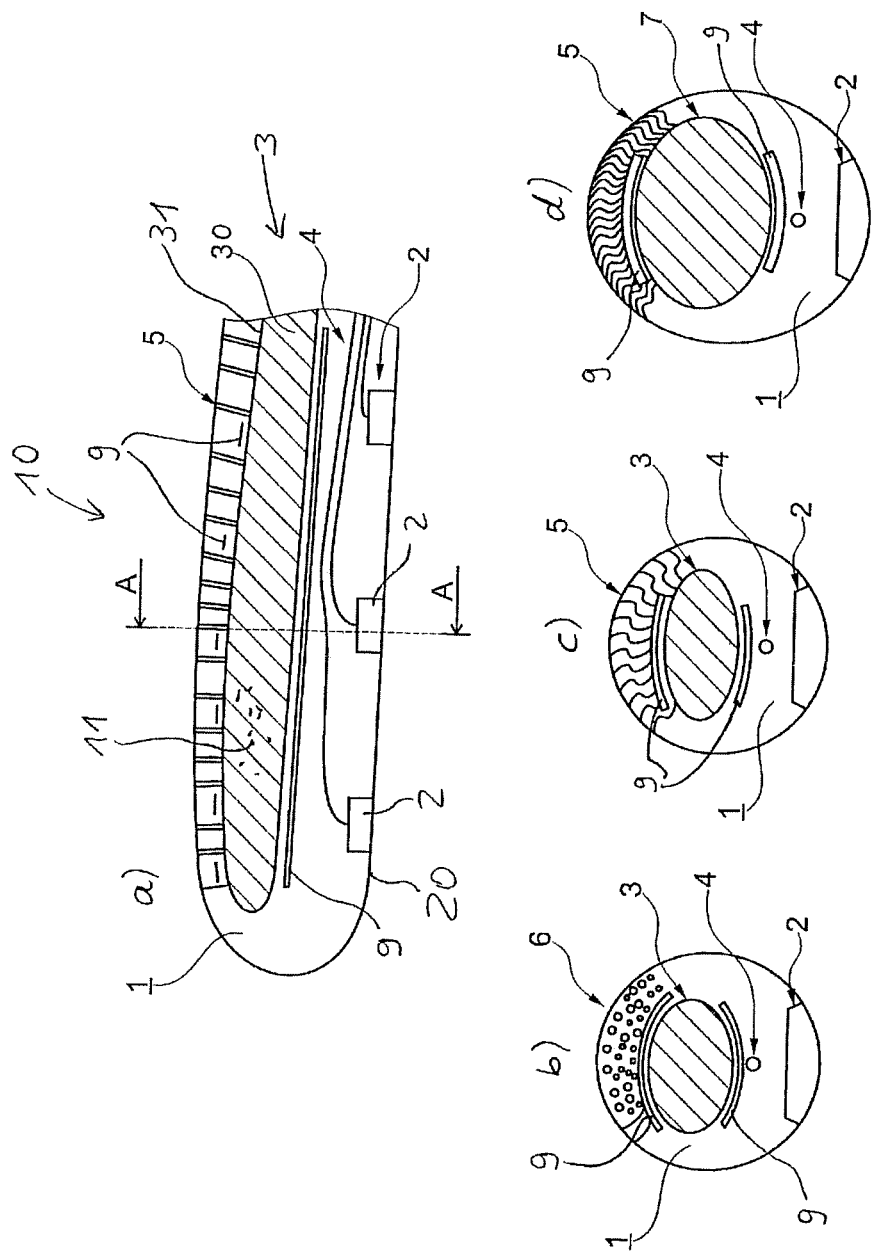
FIG. 1—shows a first embodiment of the invention and
FIG. 2—shows a second embodiment of the invention.

FIG. 1 shows, in illustration a), a shape-adaptive medical implant in the form of a cochlear implant in lateral sectional view. Illustrations b) to d) show, in accordance with the sectional plane A-A, the implant in various stages of swelling of the swellable chemical substance.

The implant 10 has a base body 1, which can be formed from silicone for example, and additionally contacts 2, electrical connecting lines 4, an actuator 3, filled with a swellable chemical substance 30 which is arranged within a flexible shell 31 of the actuator 3. The contacts 2 can form the electrodes, for example cochlea stimulation electrodes. Porous channels in the outer structure of the base body 1 are present as liquid-transport means 5. The contacts 2 and the connecting lines 4 can, for example, be formed from an inert material, for example from platinum.

Illustration a) shows a cross-section through the implant 10 in the prepared state, i.e., the implant has not yet been implanted into a body. The actuator 3 filled with the swellable chemical substance 30 is closed off from the environment by a silicone sheath formed by the base body 1. The porous channels 5 are closed off by means of a water-soluble polymer 6 which is dispersed therein and which serves as liquid-tight sealing means. As shown by illustration b), the water-soluble polymer 6 dissolves upon contact with an aqueous solution and leaves the porous channels 5, thus a fine porous structure. The porous structure serves as a permeable connection which allows supply of water from the outside into the actuator 3, but at the same time prevents escape of the hydrogel 30 from the actuator 3. As a result of the inflow of water, the hydrogel 30 and thus the entire actuator 3 swells, as depicted by reference sign 7 in illustration d). This generates self-bending of the implant and consequently an adaptive matching of the contours of the implant with a cavity in a body in which the implant was inserted.

For the use of the invention in an electrode support for cochlear implant systems, the electrode support would have to be reconstructed. The hitherto design of a partially conical silicone cylinder with platinum contacts and platinum wires embedded therein would have to be additionally extended by the swelling hydrogel actuator 3 and the selective permeable membrane. To this end, a silicone rubber with a polyelectrolytic hydrogel 30 introduced therein could be applied on the electrode structures and partially vulcanized. Thereupon, a mixture of a water-soluble powder and a silicone rubber would be applied and completely crosslinked in the next step. Owing to its demonstrated biocompatibility and swellability, a polyacrylamide supplemented with ionic groups would be suitable as polyelectrolytic hydrogel. The polyacrylamide can, for example, be supplemented with ionic groups in the form of acrylic acid groups. For the porous membrane, polyvinylpyrrolidone would be used for example.

After the implantation of the electrode support, the polyvinylpyrrolidone would dissolve in the chlorinated fluid of the inner ear (perilymph) and leave a defined pore structure 5. Ideally, the inlying hydrogel 30 would, owing to its crosslinked macroscopic structure, not be able to penetrate the pores, but water would be able to flow from the fluid of the inner ear into the hydrogel 30. With increasing water uptake by the hydrogel 30, the electrode support would snuggle up to the target structures and thus increase the contact between the targeted nerve cells and the electrode contacts.

To reduce the swelling of the hydrogel 30 in the event of a necessary explanation, it would be possible with an integrated electrical signal-delivery arrangement 9, optionally with the electrode contacts 2, to apply an electric field over the length of the electrode support. Accordingly, when using a swellable chemical substance in the form of an ionic polyacrylamide, the collapse of the hydrogel can be realized within a day with a field strength of from about 0.41 V/cm to 1.66 V/cm.

In this connection, it is not necessary for the swellable chemical substance to be completely reversibly returnable to the nonswollen state; in many applications, a partial reduction in swelling is sufficient enough.

Figure 2:
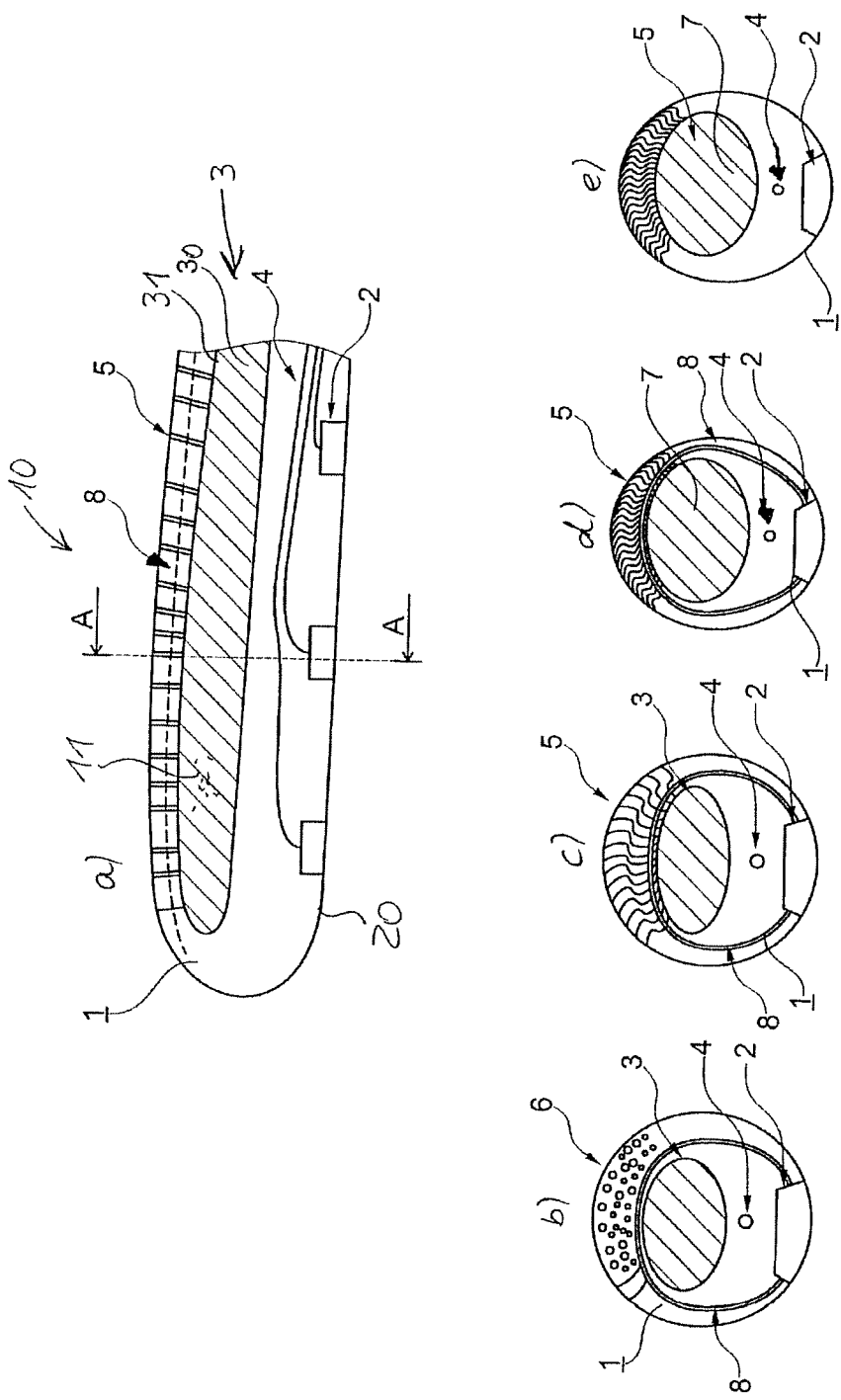

FIG. 2 shows one embodiment of the invention in which the implant 10 additionally has lateral limiting means 8, for example in the form of unidirectional reinforcement fibers close to the surface. Illustration a) shows, just as in FIG. 1, a longitudinal section through the implant 10. Illustrations b) and c) show the same states as illustrations b) and c) of FIG. 1.

In the embodiment as per FIG. 2, the implant does not have a separate electrical signal-delivery arrangement 9.

Here, the electrical signal-delivery arrangement is formed by electrically conductive fibers in the form of the reinforcement fibers 8.

Illustration d) shows the start of the swelling process of the swellable chemical substance, similar to illustration d) of FIG. 1. Via illustration e), it is clarified that the reinforcement fibers 8, which are arranged close to the surface in the base body 1 at its outer surface, limit the lateral swelling of the implant and distinctly reduce it compared with the first embodiment.

The reinforcement fibers 8 can be in the form of carbon fibers, for example having a diameter in the order of magnitude of 7 micrometers. This makes it possible to readily realize bending radii in the mid-two-digit micrometer range.

The reinforcement fibers 8 close to the surface do not substantially suppress the desired stretching in the axial direction. Accordingly, what are introduced in the base body are, for example, unidirectional fibers (warp) without cross thread (weft), which can absorb forces in the lateral direction, but not in the axial direction.

In both embodiments, a second part of the electrical signal-delivery arrangement can be formed by the contacts 2, optionally in conjunction with the connecting lines 4.

In the case of an implant having a diameter of, for example, 0.8 mm, the necessary field strength for reducing the swelling of the hydrogel can already be achieved with a voltage of 0.066 volts.

The invention claimed is:

1. A shape-adaptive medical implant comprising:
    at least one actuator for changing the implant from a first implant geometry to a second implant geometry, the implant having a different geometric shape and volume in the second implant geometry than in the first implant geometry, the at least one actuator comprising a swellable polyelectrolytic hydrogel filling for which liquid exposure is sufficient to cause swelling, the filling configured to convert from a swollen state into a non-swollen state as a consequence of supply with an electric or electromagnetic field to the filling;
    at least one stimulation electrode contact disposed in a first side of the implant;
    at least one liquid-transport means disposed in a second side of the medical implant opposite the first side, and configured to supply liquid present outside the implant to the filling, wherein the filling is enclosed within the implant between the at least one electrode contact and the liquid-transport means; and
    unidirectional conductive reinforcement fibers extending in or on the second side of the implant and configured to limit a lateral expansion of the implant, wherein the implant is configured to supply the electric or electromagnetic field to the filling through the fibers.

2. The implant as claimed in claim 1, wherein the filling contains an ionic medicament.

3. The implant as claimed in claim 1 wherein the at least one liquid-transport means has a membrane-type structure or has a form of micropores of an outer skin of the at least one actuator.

4. The implant as claimed in claim 1 wherein the liquid-soluble chemical substance is polyvinylpyrrolidone.

5. The implant as claimed in claim 1, wherein the fibers cannot absorb forces in an axial direction of the implant.

6. The implant as claimed in claim 1, wherein the fibers are carbon fibers.

7. The implant as claimed in claim 1, wherein the filling includes polyacrylamide.

8. The implant as claimed in claim 1, wherein the fibers have a linked structure.

9. The implant as claimed in claim 1, wherein the implant is in a form of a cochlear implant.

10. A method to explant the shape-adaptive medical implant of claim 1, the method comprising:
- implanting the shape-adaptive medical implant of claim 1 in a patient;
- supplying the electric or electromagnetic field to the filling through the unidirectional conductive reinforcement fibers of the implant, and thus reducing the implant in volume; and
- explanting the implant from the patient.

11. The implant as claimed in claim 1, wherein the unidirectional conductive reinforcement fibers have a fiber direction transverse to a longitudinal direction of the actuator.

\* \* \* \* \*